United States Patent [19]

Bey et al.

[11] 4,326,071
[45] Apr. 20, 1982

[54] HALOMETHYL DERIVATIVES OF GAMMA-AMINOBUTYRIC ACID AND RELATED COMPOUNDS

[75] Inventors: Philippe Bey, Strasbourg; Michel Jung, Illkirch Graffenstaden, both of France

[73] Assignee: Merrell Toraude et Compagnie, Strasbourg, France

[21] Appl. No.: 837,300

[22] Filed: Sep. 28, 1977

[51] Int. Cl.³ .................. C07C 101/10; C07C 101/18
[52] U.S. Cl. ...................................... 562/574; 544/30; 560/29; 560/30; 560/38; 560/39; 560/159; 560/161; 560/172; 562/444; 562/448; 562/449; 562/561; 564/164; 564/165; 564/197; 564/198
[58] Field of Search ................. 260/293, 86, 326.5 FL, 260/558 A, 559 A, 561 A; 560/39, 29, 30, 159, 161, 172, 38; 546/243; 564/164, 165, 197, 198; 562/444, 448, 449, 561, 574

[56] References Cited
U.S. PATENT DOCUMENTS

| | | | |
|---|---|---|---|
| 2,523,470 | 9/1950 | Kropa et al. .................. | 560/172 |
| 3,477,933 | 11/1969 | Stamm et al. ................. | 560/161 |
| 3,830,922 | 8/1974 | Witzel ........................... | 424/267 |
| 3,960,927 | 6/1976 | Metcalf et al. ............... | 260/326.5 FL |

OTHER PUBLICATIONS

March, J., *Advanced Organic Chemistry*, McGraw Hill, New York, 1968, pp. 335.

*Primary Examiner*—Richard A. Schwartz
*Attorney, Agent, or Firm*—Raymond A. McDonald; William J. Stein; John J. Kolano

[57] ABSTRACT

Novel compounds of the following general formula are useful pharmacological agents:

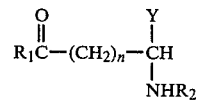

wherein Y is $FCH_2-$ or $F_2CH-$; $R_1$ is hydroxy, a straight or branched alkoxy group of from 1 to 8 carbon atoms, $-NR_{10}R_{11}$ wherein each of $R_{10}$ and $R_{11}$ is hydrogen or a straight or branched alkyl group of from 1 to 4 carbon atoms or

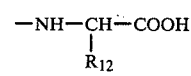

wherein $R_{12}$ is hydrogen, a straight or branched lower alkyl group of from 1 to 4 carbon atoms, benzyl or p-hydroxybenzyl; $R_2$ is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched or

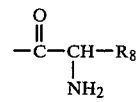

wherein $R_8$ is hydrogen, a straight or branched lower alkyl group of from 1 to 4 carbon atoms, benzyl or p-hydroxybenzyl; and n is the integer 2 or 3; pharmaceutically acceptable salts and individual optical isomers thereof.

8 Claims, No Drawings

HALOMETHYL DERIVATIVES OF GAMMA-AMINOBUTYRIC ACID AND RELATED COMPOUNDS

FIELD OF INVENTION

This invention relates to novel pharmaceutically useful α-halomethyl derivatives of γ-aminobutyric acid and related compounds which are useful pharmacological agents.

BACKGROUND OF INVENTION

Several previous studies have shown that γ-aminobutyric acid is a major inhibitory transmitter of the central nervous system as reported, for example, by Y. Godin et al., J. Neurochemistry, 16 869 (1969) and that disturbance of the excitation and inhibition interplay can lead to diseased states such as Huntington's chorea (The Lancet, Nov. 9, 1974, pp. 1122–1123), Parkinsonism, schizophrenia, epilepsy, depression, hyperkinesis and manic depression disorders, Biochem. Pharmacol. 23, 2637–2649 (1974). Certain compounds are known to elevate brain levels of γ-aminobutyric acid, for example, n-dipropylacetate (Simler et al., Biochem. Pharm. 22, 1701 (1973)) by competitively inhibiting γ-aminobutyric acid transaminase resulting in a reversible effect which lasts for only about two hours. Also, 4-aminotetrolic acid (P. M. Beart et al., J. Neurochem. 19, 1849 (1972)) is known to be a competitive reversible inhibitor of γ-aminobutyric acid transaminase. Also, α-vinyl- and α-acetylene-γ-aminobutyric acids are disclosed respectively in U.S. Pat. Nos. 3,960,927, issued June 1, 1976, and 3,959,356, issued May 25, 1976, as irreversible inhibitors of γ-aminobutyric acid transaminase.

SUMMARY OF INVENTION

The compounds of the present invention are represented by the following general formula:

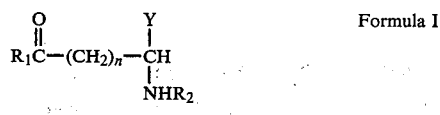

Formula I

In the above general Formula I Y is $FCH_2-$ or $F_2CH-$; $R_1$ is hydroxy, a straight or branched alkoxy group of from 1 to 8 carbon atoms, $-NR_{10}R_{11}$ wherein each of $R_{10}$ and $R_{11}$ is hydrogen or a straight or branched alkyl group of from 1 to 4 carbon atoms or

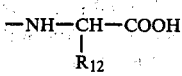

wherein $R_{12}$ is hydrogen, a straight or branched lower alkyl group of from 1 to 4 carbon atoms, benzyl or p-hydroxybenzyl; $R_2$ is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched or

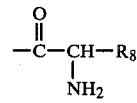

wherein $R_8$ is hydrogen, a straight or branched lower alkyl group of from 1 to 4 carbon atoms, benzyl or p-hydroxybenzyl; and n is the integer 2 or 3.

Pharmaceutically acceptable salts and individual optical isomers of the compounds of general Formula I are also included within the scope of this invention.

The compounds of general Formula I are useful pharmacological agents in that said compounds are irreversible inhibitors of γ-aminobutyric acid transaminase. Certain of the compounds of general Formula I are also useful as intermediates in the preparation of useful pharmacological agents.

DETAILED DESCRIPTION OF INVENTION

In the above general Formula I the term alkylcarbonyl is taken to mean the group

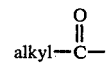

wherein the alkyl moiety has from 1 to 4 carbon atoms and is a straight chain or branched chain.

In the above general Formula I the term alkoxycarbonyl is taken to mean the group

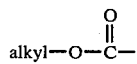

wherein the alkyl moiety has from 1 to 4 carbon atoms and is a straight chain or branched chain.

Illustrative examples of straight or branched alkyl groups having from 1 to 4 carbon atoms as used herein are methyl, ethyl, n-propyl, isopropyl, n-butyl, and tert-butyl.

Illustrative examples of straight or branched alkoxy groups having from 1 to 8 carbon atoms as used herein are methoxy, ethoxy, isopropoxy, n-butoxy, tert-butoxy, n-pentyloxy, tert-pentyloxy, n-hexyloxy and n-octyloxy.

Illustrative examples of pharmaceutically acceptable salts of the compounds of this invention include non-toxic acid addition salts formed with inorganic acids, such as hydrochloric, hydrobromic, sulfuric and phosphoric acid, and organic acids, such as, methane sulfonic, salicyclic, maleic, malonic, tartaric, citric and ascorbic acids; and non-toxic salts formed with inorganic or organic bases, such as, those of alkali metals, for example, sodium, potassium and lithium, alkaline earth metals, for example, calcium and magnesium, light metals of Group III A, for example, aluminum, organic amines, such as, primary, secondary or tertiary amines, for example, cyclohexylamine, ethylamine, pyridine, methylaminoethanol, ethanolamine and piperidine. The salts are prepared by conventional means.

Preferred compounds of this invention are those of general Formula I wherein $R_2$ is hydrogen or alkylcarbonyl wherein the alkyl moiety has from 1 to 4 carbon atoms and is straight or branched with compounds wherein $R_2$ is hydrogen being more preferred. Another preferred embodiment of this invention is the compounds of general Formula I wherein $R_1$ is hydroxy or a straight or branched alkoxy group of from 1 to 8 carbon atoms. Compounds wherein $R_1$ is hydroxy are more preferred. Also, compounds of general Formula I wherein Y is $F_2CH-$ or $FCH_2-$ are preferred. The most preferred compounds of this invention are those of general Formula I wherein $R_1$ is hydroxy, $R_2$ is hydrogen, n is the integer 2 and Y is $F_2CH-$ or $FCH_2-$.

Illustrative examples of compounds of general Formula I are the following:
 4-amino-4-fluoromethylbutyric acid,
 4-amino-4-difluoromethylbutyric acid,
 5-amino-5-fluoromethylpentanoic acid,
 5-amino-5-difluoromethylpentanoic acid,
 4-amino-4-fluoromethylbutyramide,
 N,N-dimethyl 4-amino-4-difluoromethylbutyramide,
 N-ethyl 5-amino-5-fluoromethylpentamide,
 ethyl 4-amino-4-fluoromethylbutyrate,
 isopropyl 4-amino-4-difluoromethylbutyrate,
 1-(4-amino-4-difluoromethyl-1-oxobutylamino)acetic acid,
 4-difluoromethyl-4-(1-oxoethylamino)butyric acid,
 4-fluoromethyl-4-n-propoxycarbonylaminobutyric acid, and
 methyl 4-aminomethylcarbonylaminobutyrate.

The compounds of general Formula I are useful as inhibitors of γ-aminobutyric acid transaminase resulting in an increase in brain levels of γ-aminobutyric acid rendering the compounds useful in the treatment of disorders of the central nervous system function consisting of involuntary movement associated with Huntington's chorea, Parkinsonism, extrapyramidal effects of drugs, for example, neuroleptics, seizure disorders associated with epilepsy, alcohol withdrawal, barbiturate withdrawal, psychoses associated with schizophrenia, depression, manic depression and hyperkenesis. The compounds of general Formula I are also useful as hypothermic agents, myorelaxants, cholinergic agents, antibacterial agents, anticonvulsive agents, analgesics, anorexigenic agents, antiobesity agents, tranquilizers, sedatives and central nervous system stimulants.

The ability of the compounds of general Formula I to inhibit γ-aminobutyric acid transaminase may be shown by the protective effect administration of the compound has on audiogenic seizures in mice of the DBA strain measured by the general method described by Simler et al., Biochem. Pharmacol. 22, 1701 (1973) which is currently used to evidence antiepileptic acitivity.

The compounds of this invention can be administered in various manners to achieve the desired effect. The compounds can be administered alone or in the form of pharmaceutical preparations to the patient being treated either orally or parenterally, for example, subcutaneously, intravenously or interperitoneally. The amount of novel compound administered will vary and can be any effective amount. Depending upon the patient, the condition being treated and the mode of administration, the quantity of novel compound administered may vary over a wide range to provide from about 0.1 mg/kg (milligram per kilogram) to about 300 mg/kg of body weight of the patient per day. Unit doses of these compounds can contain, for example, from about 50 mg to 2000 mg of the compounds and may be administered, for example, from 1 to 4 times daily.

As used herein the term patient is taken to mean warm blooded animals, such as, mammals, for example, cats, dogs, rats, mice, guinea pigs, sheep, horses, bovine cows and humans.

The solid unit dosage forms can be of the conventional type. Thus, the solid form can be a capsule which can be of the ordinary gelatin type containing a novel compound of this invention and a carrier, for example, lubricant and inert fillers, such as, lactose, sucrose and corn starch. In another embodiment, the novel compounds are tableted with conventional tablet bases such as lactose, sucrose or corn starch in combination with binders, such as, acacia, corn starch or gelatin, disintegrating agents, such as, corn starch, potato starch or alginic acid and a lubricant such as stearic acid or magnesium stearate. For parenteral administration the compounds may be administered as injectable dosages of a solution or suspension of a compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable or synthetic origin, for example, peanut oil, soybean oil and mineral oil. In general, water, saline, aqueous dextrose and related solutions, ethanols and glycols, such as, propylene glycol or polyethylene glycol are preferred liquid carriers, particularly for injectable solutions. The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials, such as, biodegradable polymers or synthetic silicones, for example, Silastic, silicone rubber manufactured by the Dow-Corning Corporation.

In the specific examples included hereinbelow illustrative examples of suitable pharmaceutical formulations are described.

The compounds of this invention wherein $R_1$ is hydroxy and $R_2$ is hydrogen are useful as intermediates for the preparation of cephalosporin derivatives of the following general Formula III which are useful as antibacterial agents:

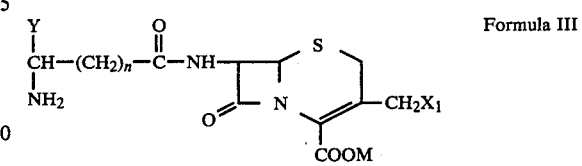

Formula III

In the above general Formula III n and Y have the meanings defined in general Formula I; M is hydrogen or a negative charge; and $X_1$ is hydrogen or acetoxy.

The compounds of general Formula III and pharmaceutically acceptable salts and individual optical isomers thereof are novel compounds useful as antibiotics and can be administered in a manner similar to that of many well known cephalosporin derivatives, for example, cephalexin, cephalothin, or cephalogylcine. The compounds of general Formula III and pharmaceutically acceptable salts and isomers thereof can be administered alone or in the form of pharmaceutical preparations either orally or parenterally and topically to warm blooded animals, that is, birds and mammals, for example, cats, dogs, bovine cows, sheep, horses and humans. For oral administration the compounds may be administered in the form of tablets, capsules or pills or in the form of elixirs or suspensions. For parenteral administration the compounds may best be used in the form of a sterile aqueous solution which may contain other solutes, for example, enough saline or glucose to make the solution isotonic. For topical administration the compounds of general Formula III, salts and isomers thereof may be incorporated into creams or ointments.

Illustrative examples of bacteria against which the compounds of general Formula III and the pharmaceutically acceptable salts and individual optical isomers thereof are active are *Staphylococcus aureus, Salmonella schotmuehleri, Klebsiella pneumoniae, Diplococcus pneumoniae* and *Streptococcus pyogenes*.

Illustrative pharmaceutically acceptable non-toxic inorganic acid addition salts of the compounds of general Formula III are mineral acid addition salts, for example, hydrogen chloride, hydrogen bromide, sulfates, sulfamates, phosphates and organic acid addition salts are, for example, maleate, acetate, citrate, oxalate, succinate, benzoate, tartrate, fumarate, malate and ascorbate. The salts can be formed by conventional means.

An illustrative example of a compound of general Formula III is 7-[[4-amino-4-difluoromethylbutyryl]amino]-3-acetyloxymethyl-8-oxo-5-thia-1-azabicyclo[4.2.0]oct-2-ene-2-carboxylic acid.

The compounds of general Formula III are prepared by coupling 7-aminocephalosporanic acid or a derivative thereof having the formula

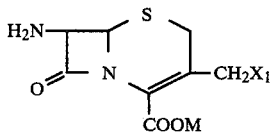

Formula IV wherein $X_1$ and M have the meanings defined in general Formula III with an acid of the formula

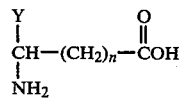

Formula V wherein Y and n have the meanings defined in general Formula I, or a functional derivative thereof, such as, the acid chloride or acid anhydride and in the presence of a dehydrating agent, such as, dicyclohexylcarbodiimide when the free acid is employed. Prior to the coupling reaction the amino group is protected with a suitable blocking group, for example, benzyloxycarbonyl which is subsequently removed by acid or base hydrolysis.

The coupling reaction is generally carried out in a solvent, such as, ethyl acetate, p-dioxane, chloroform or tetrahydrofuran in the presence of a base, such as, alkaline bicarbonate. The temperature of the reaction may vary from about −10° to 100° C., and the reaction time may vary from about ½ hour to 10 hours. The cephalosporin products are isolated by conventional procedures.

The compounds of general Formula I wherein $R_1$ is hydroxy, $R_2$ is hydrogen and Y is $FCH_2$- are prepared by treating 1 equivalent of 5-hydroxymethyl-2-pyrrolidone or 6-hydroxy-2-piperidone, as n varies from 2 to 3, with 1 equivalent of a fluoroamine reagent of the formula

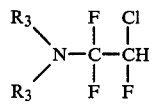

Formula VI wherein each $R_3$ is an alkyl group having from 1 to 4 carbon atoms, for example, methyl, ethyl, isopropyl, n-propyl or n-butyl followed by acid hydrolysis of the thus obtained 5-fluoromethyl-2-pyrrolidone or 6-fluoromethyl-2-piperidone. Suitable solvents for the reaction are, for example, diethyl ether, acetonitrile, tetrahydrofuran, dimethyl formamide dichloromethane or p-dioxane with reaction temperatures varying from about −20° C. to the boiling point of the reaction mixture and the reaction time varies from about 1 to 24 hours. Hydrolysis is achieved by treating 5-fluoromethyl-2-pyrrolidone or 6-fluoromethyl-2-piperidone with aqueous mineral acids, for example, hydrochloric, hydrobromic or sulfuric for about 1 to 24 hours at about 25° C. to reflux temperature.

The fluoroamine reagents of Formula VI are prepared as generally described in Org. Reactions 21, pages 158 and 159 (1974) from chlorotrifluoroethylene and an amine of the formula $(R_3)_2NH$ wherein $R_3$ has the meaning defined above.

5-Hydroxymethyl-2-pyrrolidone is known in the art. 6-Hydroxymethyl-2-piperidone may be obtained from an ester, for example, a lower alkyl, such as, methyl, ethyl, n-propyl, isopropyl or n-butyl ester, of 6-oxopiperidine-2-carboxylic acid prepared, for example, by treating the acid which is known in the art with an appropriate lower alcohol saturated with HCl gas by well known procedures. The 6-oxopiperidine-2-carboxylate is reduced to the corresponding alcohol, that is, 6-hydroxymethyl-2-piperidone by chemical reduction using a metal hydride reducing agent or by catalytic reduction. Chemical reduction is achieved using, for example, lithium aluminum hydride or lithium borohydride in a solvent, such as, diethyl ether, tetrahydrofuran, dimethyl formamide, dimethoxyethane or p-dioxane, at a temperature varying from 0° C. to the reflux temperature of the solvent for about ½ hour to 48 hours. Catalytic reduction may be achieved using copper chromite in a solvent such as p-dioxane, dimethoxyethane or lower alcohols, for example, ethanol, at a pressure of 2000 to 3000 psi with temperatures varying from about 25° to 200° C. for about 1 to 8 hours.

Compounds of general Formula I wherein $R_1$ is hydroxy, $R_2$ is hydrogen and Y is $F_2CH$- are prepared by treating 1 equivalent of 5-formyl-2-pyrrolidone or 6-formyl-2-piperidone as n varies from 2 to 3 with 1 to 10 equivalents of an N,N-disubstituted aminosulfur trifluoride of the formula

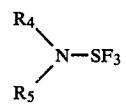

Formula VII optionally in the presence of a solvent, such as, diethyl ether, tetrahydrofuran, benzene, acetonitrile, p-dioxane, dimethoxyethane, dichloromethane or mixtures thereof at a temperature of about −20° C. to the boiling point of the solvent for about 10 minutes to 24 hours followed by acid hydrolysis. Hydrolysis is achieved by treating the thus obtained 5-difluoromethyl-2-pyrrolidone or 6-difluoromethyl-2-piperidone with aqueous mineral acid, for example, hydrochloric, hydrobromic or sulfuric at a temperature of about 25° C. to reflux temperature for about 1 to 24 hours.

The N,N-disubstituted aminosulfur trifluorides of Formula VII are known in the art, for example, see Synthesis 1973, p. 788 or may be obtained by reacting an appropriate secondary amine with sulfur (IV) fluoride by procedures generally known in the art.

5-Formyl-2-pyrrolidone and 6-formyl-2-piperidone are obtained respectively by oxidation of 5-hydroxymethyl-2-pyrrolidone or 6-hydroxymethyl-2-piperidone or by reduction of 5-oxopyrrolidine-2-carboxylic acid or 6-oxopiperidine-2-carboxylic acid or lower alkyl esters of said acids by procedures generally known in the art. For example, oxidation of the hydroxymethyl derivatives to the corresponding aldehydes may be achieved using pyridinium chlorochromate (Tetrahedron Lett. 1975, 2647); Collins' reagent, that is, a pyridine chromate complex (Tetrahedron Lett. 1968, 3363); a dichloro dimethylsulfide complex (J. Am. Chem. Soc. 94, 7586 (1972)) or a complex of N-chlorosuccinimide or N-bromosuccinimide with dimethylsulfide; or silver carbonate on celite (C.R. Acad. Science, Paris 267, 900 (1968)). Reduction of the acids, or esters thereof, to the corresponding aldehydes may be achieved by electrolytic reduction (Bull. Soc. Chim. Japan 25, 404 (1952)); using diisobutylaluminum hydride (J. Org. Chem. 31, 1447 (1966)); or tributyloxylithium aluminum hydride (J. Org. Chem. 35, 458 (1970)).

The compounds of general Formula I wherein $R_1$ is hydroxy, $R_2$ is hydrogen and Y is $F_3C$- are prepared by reducing a ketone of the formula

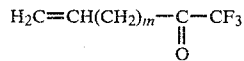   Formula VIII wherein m is the integer 2 or 3 as n varies from 2 to 3 in the compounds of Formula I, to the corresponding alcohol treating 1 equivalent of said alcohol with 1 equivalent of an imide, such as, phthalimide, succinimide or maleimide, 1.1 equivalents of a phosphine, for example, triphenylphosphine or a trialkylphosphine, such as, tri-n-butylphosphine and 1.1 equivalents of diethyl azodicarboxylate in a solvent, such as, ethers, for example, diethyl ether, tetrahydrofuran or p-dioxane or benzene or dimethoxyethane at about 0° to 100° C., preferably about 25° C., for about ½ hour to 24 hours under an inert atmosphere, such as nitrogen or argon, oxidizing the thus formed imide derivative, that is, 1-trifluoromethyl-1-imidopent-4-ene or 1-trifluoromethyl-1-imidohex-5-ene to the corresponding acid, namely 4-trifluoromethyl-4-imidopentanoic acid and hydrolyzing the imido-acid derivatives to the corresponding free amines.

Reduction of the appropriate ketone of Formula VIII to the corresponding alcohol is achieved chemically using, for example, 1 to 10 equivalents of a metal hydride reducing ragent, such as lithium borohydride, sodium borohydride, sodium cyanoborohydride, or lithium aluminum hydride, borane or dimethylthioborane or catalytically using, for example, Raney nickel, rhodium, palladium on charcoal, or platinum oxide. Overall the reaction time varies from about 10 minutes to 24 hours and the temperature varies from about −40° to 100° C. depending on the reducing reagent employed. When chemical reduction is employed the reaction time generally varies from about 10 minutes to 24 hours with temperatures varying from about −40° to 65° C. Suitable solvents for chemical reduction of compounds of general Formula VIII include lower alcohols, such as, methanol or ethanol or ethers, such as, diethyl ether or tetrahydrofuran. When catalytic reduction is employed the reaction time varies from about 1 hour to 24 hours, the reaction temperature varies from about 25° to 100° C. and the pressure varies from 1 to 120 atmospheres. Suitable solvents for catalytic reduction of compounds of general Formula VIII include lower alcohols, for example, methanol or ethanol, acetic acid, or ethyl acetate. Chemical reduction is preferred.

Oxidation of the 1-imido-1-trifluoromethylalkene derivatives to the corresponding acids is achieved using any oxidizing agent known in the art to oxidatively cleave double bonds, for example, ozone, sodium metaperiodate and potassium permanganate, potassium permanganate alone, osmium tetroxide and potassium permanganate or ruthenium tetroxide and sodium metaperiodate. The oxidation is carried out in solvents, such as, dichloromethane, carbon tetrachloride, p-dioxane, tetrahydrofuran, diethyl ether, acetone, pyridine, water or mixtures thereof at a pH of about 7 to 10 with temperatures varying from 0° to 80° C. for about 1 to 24 hours.

Hydrolysis of the imide to the amine is achieved using a strong mineral acid, for example, hydrochloric acid, hydrobromic acid or sulfuric acid or an organic acid, for example, toluene sulfonic acid or trifluoroacetic acid in water at reflux temperature for about 4 to 48 hours, or using, for example, 1 to 3 equivalents of hydrazine, methylhydrazine or methylamine at a temperature of from about 25° C. to reflux for about 1 to 12 hours followed by treatment wih a strong mineral acid or organic acid as described above.

The compounds of general Formula VIII are prepared by treating an alkenyl halide of the formula

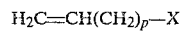   IX wherein p is the integer 2 or 3 as m varies from 2 to 3 in the compounds of Formula VIII and X is halogen, such as, chlorine, bromine or iodine with triphenylphosphine in a suitable solvent, such as, hydrocarbons, for example, benzene or toluene, or lower alcohols, such as, methanol or ethanol, or acetonitrile, tetrahydrofuran, diethyl ether or dimethoxyethane at about 25° C. to the reflux temperature of the solvent for about 10 minutes to 48 hours. On cooling a precipitate forms which is washed with solvent and recrystallized using, for example, ethyl acetate, acetonitrile or a lower alcohol, such as methanol or ethanol to give the appropriate alkenyl triphenylphosphonium salt which is added to excess (up to 25%) sodium or lithium metal dissolved in liquid ammonia to which is added a catalytic amount of ferric nitrate with stirring for about 10 minutes to 3 hours after which the ammonia is evaporated under an inert atmosphere, such as, nitrogen or argon. An appropriate solvent, such as, benzene, toluene, diethyl ether, tetrahydrofuran or dimethoxyethane is added and the resulting alka-dienylene phosphorane is collected. The alka-dienylenephosphorane is treated with an ester of, such as, a lower alkyl, for example, methyl, ethyl, n-propyl, isopropyl or n-butyl ester of trifluoroacetic acid in a solvent such as benzene, toluene, diethyl ether, tetrahydrofuran or dimethoxyethane under an inert atmosphere such as nitrogen or argon at a temperature of about 0° C. to the reflux temperature of the solvent for about 30 minutes to 24 hours after which the reaction mixture is concentrated and distilled to give the appropriate 1-alkoxy-1-trifluoromethylpent-1,4-diene and 1-alkoxy-1-trifluoromethylhex-1,5-diene. The appropriate diene is treated with aqueous mineral acid, such as, hydrochloric or hydrobromic acid or an organic acid, such as, trifluoroacetic acid or p-toluenesulfonic acid using a cosolvent, such as, tetrahydrofuran, diethyl ether or benzene for about 30 minutes to 24 hours at a temperature of from about 0° C. to the reflux temperature of the solvent to give the appropriate ketone. The amount of acid employed may vary from a catalytic amount to concentrated acid.

Alternatively the compound of general Formula I wherein $R_1$ is hydroxy, $R_2$ is hydrogen, Y is $F_3C$- and n is 2 may be obtained by reducing an ester, for example, a lower alkyl, such as, methyl, ethyl, n-propyl, isopropyl or n-butyl ester of levulinic acid, that is, 5,5,5-trifluoro-4-oxopentanoic acid, to the corresponding alcohol, treating 1 equivalent of said alcohol with 1 equivalent of an imide, such as, phthalimide, succinimide or maleimide, 1.1 equivalents of a phosphine, for example, triphenylphosphine or a trialkylphosphine, such as, tri-n-butylphosphine and 1.1 equivalents of diethyl azodicarboxylate in a solvent, such as, ethers, for example, diethyl ether, tetrahydrofuran or p-dioxane or benzene or dimethoxyethane at about 0° to 100° C., preferably about 25° C., for about ½ hour to 24 hours under an inert atmosphere, such as, nitrogen or argon and hydrolyzing the thus formed imide to the corresponding free amine.

Reduction of the appropriate ester of levulinic acid to the corresponding alcohol is achieved chemically using, for example, 1 to 10 equivalents of a metal hydride reducing reagent, such as lithium borohydride, sodium borohydride, sodium cyanoborohydride, or lithium aluminum hydride, borane or dimethylthioborane or catalytically using, for example, Raney nickel, rhodium, palladium on charcoal, or platinum oxide. Overall the reaction time varies from about 10 minutes to 24 hours and the temperature varies from about −40° to 100° C. depending on the reducing reagent employed. When chemical reduction is employed the reaction time generally varies from about 10 minutes to 24 hours with temperatures varying from about −40° to 65° C. Suitable solvents for chemical reduction of the ester include lower alcohols, such as, methanol or ethanol or ethers, such as, diethyl ether or tetrahydrofuran. When catalytic reduction is employed the reaction time varies from about 1 hour to 24 hours, the reaction temperature varies from about 25° to 100° C. and the pressure varies from 1 to 120 atmospheres. Suitable solvents for catalytic reduction of the appropriate ester of levulinic acid include lower alcohols, for example, methanol or ethanol, acetic acid, or ethyl acetate. Catalytic reduction is preferred.

Hydrolysis of the imide to the amine is achieved using a strong mineral acid, for example, hydrochloric acid, hydrobromic acid or sulfuric acid or an organic acid, for example, toluene sulfonic acid or trifluoroacetic acid in water at reflux temperature for about 4 to 48 hours or using, for example, 1 to 3 equivalents of hydrazine, methylhydrazine or methylamine at a temperature of from about 25° C. to reflux for about 1 to 12 hours followed by treatment with a strong mineral acid or organic acid as described above.

As indicated hereinabove tri-alkylphosphines, such as, tri-n-butylphosphine, may be employed in preparing compounds of general Formula I wherein Y is $F_3C$-. As used in the name tri-alkylphosphine the alkyl moiety has from 1 to 10 carbon atoms. The tri-alkylphosphines are known in the art or may be prepared by procedures generally known in the art.

The compounds of general Formula I wherein $R_2$ is alkylcarbonyl wherein the alkyl moiety is straight or branched and has from 1 to 4 carbon atoms are prepared by treating the corresponding derivatives wherein $R_2$ is hydrogen with the acid halide of the formula

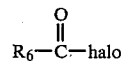

wherein halo is a halogen atom, for example, chlorine or bromine and $R_6$ is a straight or branched alkyl group having from 1 to 4 carbon atoms in water in the presence of a base such as sodium hydroxide or triethylamine at a temperature of from 0° C. to 25° C. for from ½ hour to 6 hours.

The compounds of general Formula I wherein $R_2$ is alkoxycarbonyl wherein the alkoxy moiety is straight or branched and has from 1 to 4 carbon atoms are prepared by treating the corresponding derivative wherein $R_2$ is hydrogen with an alkyl haloformate of the formula

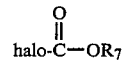

wherein halo is a halogen atom such as chlorine or bromine and $R_7$ is a straight or branched alkyl group having from 1 to 4 carbon atoms in water in the presence of a base such as sodium hydroxide or triethylamine at a temperature of from about 0° to 25° C. for from about ½ hour to 6 hours.

The compounds of general Formula I wherein $R_2$ is

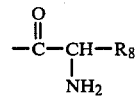

wherein $R_8$ is hydrogen, a straight or branched lower alkyl group of from 1 to 4 carbon atoms, benzyl or p-hydroxybenzyl are prepared by treating the corresponding derivative wherein $R_2$ is hydrogen and $R_1$ is a lower alkoxy group with an acid of the formula

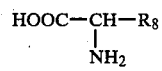

or an anhydride thereof wherein the amino group is protected with a suitable blocking group such as benzyloxycarbonyl or tert-butoxycarbonyl and $R_8$ has the meaning defined hereinabove in an ether, such as, tetrahydrofuran or dioxane, methylene chloride or chloroform and in the presence of a dehydrating agent when the free acid is employed, at a temperature of from about 0° C. to 35° C. for about 1 to 12 hours followed by acid hydrolysis to remove the protecting groups.

The compounds of general Formula I wherein $R_1$ is a straight or branched alkoxy group of from 1 to 8 carbon atoms are prepared by treating the corresponding derivatives wherein $R_1$ is hydroxy with thionyl chloride to form the acid chloride which is reacted with an alcohol of the formula $R_9$-OH, wherein $R_9$ is a straight or branched alkyl group of from 1 to 8 carbon atoms, such as, methyl, ethyl, n-propyl, isopropyl, n-butyl, hexyl, or octyl, at about 25° C. for from about 4 to 12 hours.

The compounds of general Formula I wherein $R_1$ is $-NR_{10}R_{11}$ wherein each of $R_{10}$ and $R_{11}$ is hydrogen or a straight or branched lower alkyl of 1 to 4 carbon atoms are prepared by an acylation reaction of an acid halide, for example, an acid chloride, or the corresponding compound wherein $R_1$ is hydroxy and $R_2$ has the meaning defined in Formula I with the proviso that any free amino group is protected with a suitable protecting group, for example, carbobenzyloxy or tert-butoxycarbonyl with an excess of an appropriate amine which may be represented as $HNR_{10}R_{11}$. The reaction is carried out in methylene chloride, chloroform, dimethylformamide, ethers such as tetrahydrofuran or dioxane or benzene at about 25° C. for about 1 to 4 hours. Suitable amines are, for example, ammonia, or a compound which is a potential source of ammonia, for example, hexamethylenetetramine; primary amines, for example, methylamine, ethylamine, or n-propylamine; and secondary amines such as dimethylamine, diethylamine or di-n-butylamine. Following the acylation reaction the amino protecting group is removed by treatment with acid, for example, hydrogen bromide in dioxane or hydrogenolysis.

The compounds of general Formula I wherein $R_1$ is

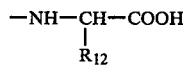

are prepared by reacting the corresponding derivative wherein $R_1$ is hydroxy or a functional derivative thereof such as an acid anhydride and $R_2$ has the meaning defined in Formula I with the proviso that any free amino group is protected with a suitable blocking group, such as benzyloxycarbonyl or tert-butoxycarbonyl with a compound of the formula

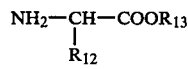

wherein $R_{12}$ has the meaning defined in general Formula I and $R_{13}$ is a lower alkyl group, for example, methyl or ethyl in an ether, such as, tetrahydrofuran or dioxane at 0° to about 50° C. for about 1 to 24 hours followed by acid hydrolysis to remove the protecting group, with the proviso that when the amine protected free acid is employed the reaction is carried out using a dehydrating agent such as dicyclohexylcarbodiimide.

The individual optical isomers of the compounds of general Formula I wherein $R_2$ is H may be separated by using a (+) or (−) binaphthylphosphoric acid salt by the method of R. Viterbo et al., Tetrahedron Letters 48, 4617 (1971). Other resolving agents such as (+) camphor-10-sulfonic acid may also be employed. The individual optical isomers of compounds of Formula I wherein $R_2$ is other than H may be obtained as described herein for the racemate only starting with the resolved amine.

The lactams of this invention as represented by general Formula II are prepared by generally known procedures from the appropriate amino acid of the formula

wherein n and Y have the meanings defined in general Formula I. The lactams may be obtained, for example, by treating an acid of Formula X with a dehydrating agent, such as, dicyclohexylcarbodiimide or by heating an ester, such as, a lower alkyl, for example, ethyl ester of the acid of Formula X in a lower alcohol solvent for about 1 to 24 hours at about 80° to 120° C.

EXAMPLE 1

7-[[4-Amino-4-fluoromethylbutyryl]amino]-3-acetyloxymethyl-8-oxo-5-thia-1-azabicyclo[4.2.0]oct-2-ene-2-carboxylic acid A mixture of 1 g of 3-acetyloxy-7-amino-8-oxo-5-thia-1-azabicyclo[4.2.0]oct-2-ene-2-carboxylic acid and 1 g of 4-amino-4-fluoromethylbutyric acid chloride wherein the free amino group is protected with tert-butoxycarbonyl in 50 ml of ethyl acetate is refluxed for two hours after which the solvent is removed leaving a residue which is treated with mild acid and chromatographed on silica gel using benzene-acetone as the eluant to give 7-[[4-amino-4-fluoromethylbutyryl]amino]-3-acetyloxymethyl-8-oxo-5-thia-1-azabicyclo[4.2.0]oct-2-ene-2-carboxylic acid.

EXAMPLE 2

An illustrative composition for hard gelatin capsules is as follows:

| (a) | 4-amino-4-fluoromethylbutyric acid | 20 mg |
|---|---|---|
| (b) | talc | 5 mg |
| (c) | lactose | 90 mg |

The formulation is prepared by passing the dry powders of (a) and (b) through a fine mesh screen and mixing them well. The powder is then filled into hard gelatin capsules at a net fill of 115 mg per capsule.

EXAMPLE 3

An illustrative composition for tablets is as follows:

| (a) | 4-amino-4-difluoromethylbutyric acid | 20 mg |
|---|---|---|
| (b) | starch | 43 mg |
| (c) | lactose | 45 mg |
| (d) | magnesium stearate | 2 mg |

The granulation obtained upon mixing the lactose with the compound (a) and part of the starch and granulated with starch paste is dried, screened, and mixed with the magnesium stearate. The mixture is compressed into tablets weighing 110 mg each.

EXAMPLE 4

An illustrative composition for an injectable suspension is the following 1 ml ampul for an intramuscular injection.

|   |   | Weight percent |
|---|---|---|
| (a) | 4-amino-4-difluoromethylbutyric acid | 1.0 |
| (b) | polyvinylpyrrolidone | 0.5 |
| (c) | lecithin | 0.25 |
| (d) | water for injection to make | 100.0 |

The materials (a)-(d) are mixed, homogenized, and filled into 1 ml ampuls which are sealed and autoclaved 20 minutes at 121° C. Each ampul contains 10 mg per ml of novel compound (a).

EXAMPLE 5

4-Amino-4-fluoromethylbutyric acid

To a solution of 0.8 g (6.2 mmole) of 5-hydroxymethyl-2-pyrrolidone in a mixture of 20 ml of tetrahydrofuran and acetonitrile is added a solution of 1.2 g (6.4 mmole) of 2-chloro-1,1,-trifluorotriethylamine in 10 ml of tetrahydrofuran during ½ hour. The reaction mixture is allowed to stand at about 25° C. for 15 hours after which the solution is washed with water, potassium hydroxide until neutral, water and then dried over magnesium sulfate and filtered. The filtrate is evaporated under reduced pressure leaving a residue which is distilled under high vacuum to afford 5-fluoromethyl-2-pyrrolidone. The pyrrolidone (500 mg) is heated in 20 ml of 6 N hydrochloric acid at reflux for 12 hours after which the solution is concentrated under vacuo and the residue passed through an Amberlite column IR 120 H+. Elution with 1 M ammonium hydroxide affords 4-amino-4-fluoromethylbutyric acid which is recrystallized from water/acetone.

EXAMPLE 6

4-Amino-4-difluoromethylbutyric acid (A) To a suspension of 15 mmole of pyridinium chlorochromate in 20 ml of methylene chloride is rapidly added at 25° C. a suspension of 10 mmole of 5-hydroxymethyl-2-pyrrolidone in 10 ml of acetonitrile. The mixture is stirred for 10 hours at 25° C. then diluted with diethyl ether. Filtration of the organic phase through florisil and concentration of the solvent at reduced pressure affords 5-formyl-2-pyrrolidone.

(B) To a solution of 0.07 mole of dimethylaminosulfur trifluoride in 30 ml of dioxane is added dropwise with stirring a solution of 0.01 mole of 5-formyl-2-pyrrolidone in 10 ml of dioxane. Stirring is continued for 15 hours at 25° C. after which the reaction mixture is poured into ice water then extracted with ethyl acetate. The organic phase is separated, washed with water, dried over magnesium sulfate, filtered and concentrated under reduced pressure to yield 5-difluoromethyl-2-pyrrolidone.

(C) When in the procedure of Example 5 500 mg of 5-difluoromethyl-2-pyrrolidone is substituted for 5-fluoromethyl-2-pyrrolidone, 4-amino-4-difluoromethylbutyric acid is obtained.

EXAMPLE 7

4-Amino-4-trifluoromethylbutyric acid

A mixture of 20 ml of 1-bromo-3-butyne and 25 mmole of tirphenylphosphine in 50 ml of benzene is heated at reflux for 3 days. The solid which separates upon cooling is filtered, washed with benzene and dried under reduced pressure is afford triphenyl-3-butenylphosphonium bromide. To a solution of 100 ml of liquid ammonia is added 0.26 g of finely divided sodium and a catalytic amount of ferric nitrate. When the blue solution turns gray finely powdered triphenyl-3-butenylphosphonium bromide ($2.10^{-2}$ mole) is added. The reaction mixture is stirred for 15 minutes after which the ammonia is evaporated under a stream of nitrogen. To the resulting residue is added 100 ml of benzene, and the heterogeneous mixture is heated at reflux temperature for 10 minutes. The solid residue is filtered off and the filtrate is evaporated to dryness to give 3-butenylidenephosphorane. To a solution of salt free 3-butenylidenephosphorane ($2.10^{-2}$ mole) in 100 ml of benzene is added 6.6 g ($5.10^{-2}$ mole) of ethyl trifluoroacetate. The reaction mixture is heated at reflux temperature for 12 hours under nitrogen. Concentration of the solvent leaves an oily residue which is purified by distillation to give 1-trifluoromethyl-1-ethoxy-1,4-pentadiene. A suspension of 10 g of 1-trifluoromethyl-1-ethoxy-1,4-pentadiene in 20 ml of 1 N aqueous sulfuric acid is stirred for 20 minutes. Continuous extraction of the mixture with ether affords 1-trifluoromethylpent-4-ene-1-one.

A solution of 15.2 g of 1-trifluoromethylpent-4-ene-1-one in 150 ml of methanol is heated at 0° C. with 1.7 g of sodium borohydride. The reaction mixture is stirred for 2 hours at 25° C. then neutralized with HCl. The residue obtained after evaporation of the solvent is extracted several times with chloroform, washed with brine, dried over magnesium sulfate and concentrated under reduced pressure to give 1-trifluoromethylbut-4-ene-1-ol. A solution of 10 mmole of 1-trifluoromethylbut-4-ene-1-ol, 10 ml of triphenylphosphine and 10 ml of diethyl azodicarboxylate in 25 ml of tetrahydrofuran is stirred under nitrogen at 25° C. for 16 hours after which the solvent is evaporated under reduced pressure. The resulting residue is treated with benzene. The insoluble material is discarded and the semi-solid obtained after concentration of the filtrate under reduced pressure is recrystallized from methylene chloride-pentane to afford N-(1-trifluoromethyl-3-butenyl)phthalimide. To a solution of 25 mmole of the phthalimide in 25 ml of dioxane is added a solution of 12 mmole of potassium permanganate and 50 mmole of sodium metaperiodate in water. Potassium carbonate is added to adjust the pH of the solution to 8 and the reaction mixture is stirred for 24 hours at 25° C. then acidified with sulfuric acid to a pH of 1 and extracted with ethyl acetate. The organic phase is washed with brine, dried over magnesium sulfate and concentrated under reduced pressure. The resulting residue is recrystallized from methylene chloride-pentane to give 4-trifluoromethyl-4-phthalimidopentanoic acid. A solution of 20 ml of 4-trifluoromethyl-4-phthalimidopentanoic acid and 20 mmole of hydrazine hydrate in 20 ml of ethanol is heated at reflux temperature for 12 hours. The solid which separates on cooling is filtered and washed with water. The filtrate is concentrated under reduced pressure to give a solid which is recrystallized from water/acetone to give 4-amino-4-trifluoromethylpentanoic acid.

EXAMPLE 8

4-Amino-4-trifluoromethylbutyric acid

To a solution of 30 mmole of 4-trifluoromethyl-4-oxobutyric acid ethyl ester in 20 ml of ethanol cooled to 0° C. is added 30 mmole of sodium borohydride. The reaction mixture is stirred at 0° C. for 4 hours then acidified with M HCl to a pH of 1. The solvent is evaporated under reduced pressure and the residue is partitioned between water and ether. The organic phase is washed with brine, dried over magnesium sulfate and concentrated to give 4-trifluoromethyl-4-hydroxybutyric acid ethyl ester. A mixture of 20 mmole of 4-trifluoromethyl-4-hydroxybutyric acid ethyl ester, 22 mmole of triphenylphosphine, 20 mmole of phthalimide and 22 mmole of diethyl azodicarboxylate in 60 ml of tetrahydrofuran is heated at reflux temperature under nitrogen for 24 hours. The solvent is evaporated under reduced pressure, and the residue chromatographed on silica gel to give 4-trifluoromethyl-4-phthalimidobutyric acid ethyl ester. A suspension of 30 mmole of 4-trifluoromethyl-4-phthalimidobutyric acid ethyl ester in 20 ml of concentrated HCl is heated at reflux temperature for 24 hours. The solid which separates on cooling is filtered, and the filtrate concentrated under reduced pressure. The residue is dissolved in the minimum quantity of water, and the pH of the solution adjusted to 5 by the addition of sodium hydroxide. Acetone is added, and the precipitated 4-amino-4-trifluoromethylbutyric acid collected by filtration.

EXAMPLE 9

5-Amino-5-fluoromethylpentanoic acid

When in the procedure of Example 5 an appropriate amount of 6-hydroxymethyl-2-piperidone is substituted for 5-hydroxymethyl-2-pyrrolidone, 5-amino-5-fluoromethylpentanoic acid is obtained.

EXAMPLE 10

5-Amino-5-difluoromethylpentanoic acid

When in the procedure of Example 6 (A) an appropriate amount of 6-hydroxymethyl-2-piperidone is substituted for 5-hydroxymethyl-2-pyrrolidone, 6-formyl-2-piperidone is obtained. When an appropriate amount of 6-formyl-2-piperidone is substituted for 5-formyl-2-pyrrolidone in the procedure of Example 6 (B), 6-difluoromethyl-2-piperidone is obtained which, when substituted for 5-difluoromethyl-2-pyrrolidone in an appropriate amount in the procedure of Example 5, yields 5-amino-5-difluoromethylpentanoic acid.

EXAMPLE 11

4-Difluoromethyl-4-(1-oxoethylamino)butyric acid

To a solution of 2 mmole of 4-amino-4-difluoromethylbutyric acid in 5 ml of 1 N sodium hydroxide at 0° C. are added simultaneously from two syringes 160 mg of acetyl chloride diluted in 1 ml of dioxane and 2 ml of 1 N sodium hydroxide. After 30 minutes at 0° C. the solution is acidified by the addition of 6 N hydrochloric acid, then extracted well with dichloromethane. The organic phase is dried and concentrated to afford 4-difluoromethyl-4-(1-oxoethylamino)butyric acid.

EXAMPLE 12

N-Propyl 4-amino-4-difluoromethylbutyramide hydrobromide

To a solution of 2 mmole of 4-amino-4-difluoromethylbutyric acid in 5 ml of 1 N sodium hydroxide at 0° C. are added simultaneously from two syringes 2 mmole of benzyl chloroformate in 1 ml of dioxane and 2 ml of 1 N sodium hydroxide. After 30 minutes at 0° C. the solution is acidified by the addition of 6 N hydrochloric acid, then extracted well with dichloromethane. The organic phase is dried and concentrated to afford 4-benzyloxycarbonylamino-4-difluoromethylbutyric acid which is dissolved in 15 ml of dichloromethane and treated with 2 mmole of thionyl chloride at 25° C. for 1 hour after which 4 mmole of propyl amine is added. The solution is stirred at 25° C. for one hour, then washed with water, dried and concentrated. The residue is treated with 6 ml of a solution of dioxane containing 40% w/w hydrogen bromide and allowed to stand for 30 minutes at 25° C. after which 50 ml of ether is added. The resulting precipitate is collected to afford N-propyl 4-amino-4-difluoromethylbutyramide hydrobromide.

EXAMPLE 13

4-Amino-4-difluoromethylbutyric acid ethyl ester

A solution of 2 mmole of 4-amino-4-difluoromethylbutyric acid in 15 ml of dichloromethane is treated with 2 mmole of thionyl chloride at 25° C. for one hour after which 20 ml of ethanol is added. The solution is stirred at 25° C. for one hour, washed with water, dried and concentrated to afford 4-amino-4-difluoromethylbutyric acid ethyl ester.

EXAMPLE 14

4-(2-Aminopropionylamino)-4-difluoromethylbutyric acid

A solution of 1 mmole of 4-amino-4-difluoromethylbutyric acid ethyl ester in 4 ml of methylene chloride is treated with 1 mmole of N-carbobenzoxyalanine and 1 mmole of N,N'-dicyclohexylcarbodiimide for 10 hours at 25° C. The mixture is cooled to 0° C. and the precipitated dicyclohexylurea filtered off. The filtrate is diluted with methylene chloride, washed with water, bicarbonate, dilute HCl then dried and concentrated. The residue is treated with 5 ml of ethanol and 5 ml of a 40% (w/w) solution of hydrogen bromide in dioxane for 30 minutes at 25° C. Ether (50 ml) is added and the resulting precipitate collected which is treated with 15 ml of 1 N sodium hydroxide for 10 hours at 25° C. The pH of the solution is adjusted to neutral, and the product isolated from an Amberlite 120 H+ resin by elution with 2 M ammonium hydroxide affording 4-(2-aminopropionylamino)-4-difluoromethylbutyric acid.

We claim:

1. A compound of the formula

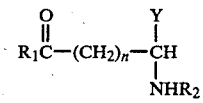

wherein Y is FCH$_2$- or F$_2$CH-; R$_1$ is hydroxy, a straight or branched alkoxy group of from 1 to 8 carbon atoms, -NR$_{10}$R$_{11}$ wherein each of R$_{10}$ and R$_{11}$ is hydrogen or a straight or branched alkyl group of from 1 to 4 carbon atoms or

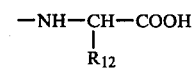

wherein R$_{12}$ is hydrogen, a straight or branched lower alkyl group of from 1 to 4 carbon atoms, benzyl or p-hydroxybenzyl; R$_2$ is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched or

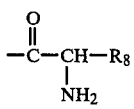

wherein $R_8$ is hydrogen, a straight or branched lower alkyl group of from 1 to 4 carbon atoms, benzyl or p-hydroxybenzyl; n is the integer 2 or 3; or a pharmaceutically acceptable salt or an individual optical isomer thereof.

2. A compound of claim 1 wherein $R_2$ is hydrogen or alkylcarbonyl.

3. A compound of claim 1 wherein $R_2$ is hydrogen.

4. A compound of claim 1 wherein $R_1$ is hydroxy or a straight or branched alkoxy group of from 1 to 8 carbon atoms.

5. A compound of claim 1 wherein $R_1$ is hydroxy.

6. A compound of claim 1 wherein Y is $F_2CH-$ or $FCH_2-$.

7. A compound of claim 1 wherein n is the integer 2.

8. A compound of claim 1 wherein $R_1$ is hydroxy, $R_2$ is hydrogen, n is 2 and Y is $F_2CH-$ or $FCH_2-$.

* * * * *